United States Patent
Kunimoto et al.

(10) Patent No.: US 11,058,660 B2
(45) Date of Patent: Jul. 13, 2021

(54) EXTERNAL WOUND-HEALING AGENT, AND EXTERNAL WOUND-HEALING MATERIAL

(71) Applicant: Mitsui Chemicals, Inc., Tokyo (JP)

(72) Inventors: Naosuke Kunimoto, Sodegaura (JP); Kenichi Suzuki, Sodegaura (JP); Kouya Kojima, Sodegaura (JP); Akira Hasegawa, Sodegaura (JP); Yasufumi Tsuchiya, Sodegaura (JP); Jun Kamada, Sodegaura (JP); Satoshi Yamasaki, Sodegaura (JP); Goro Kuwamura, Sodegaura (JP); Daisuke Hasegawa, Sodegaura (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 16/236,752

(22) Filed: Dec. 31, 2018

(65) Prior Publication Data
US 2019/0133987 A1    May 9, 2019

Related U.S. Application Data (62) Division of application No. 15/326,150, filed as application No. PCT/JP2015/070302 on Jul. 15, 2015, now abandoned.

(30) Foreign Application Priority Data

Jul. 15, 2014   (JP) .................................. 2014-145189

(51) Int. Cl.
*A61K 31/23*    (2006.01)
*A61P 17/02*    (2006.01)
(Continued)

(52) U.S. Cl.
CPC ............ *A61K 31/23* (2013.01); *A61K 9/0092* (2013.01); *A61K 9/7007* (2013.01); *A61K 47/32* (2013.01);
(Continued)

(58) Field of Classification Search
CPC ........ A61K 31/23; A61K 9/7007; A61P 17/02
See application file for complete search history.

(56) References Cited

U.S. PATENT DOCUMENTS 2,804,424 A * 8/1957 Stirn .................... A61L 15/46
424/446
6,762,339 B1 7/2004 Klun et al.
(Continued)

FOREIGN PATENT DOCUMENTS

CN    104306212 A    1/2015
EP    1304102 A2    4/2003
(Continued)

OTHER PUBLICATIONS

International Search Report (PCT/ISA/210) dated Sep. 15, 2015, by the Japan Patent Office as the International Searching Authority for International Application No. PCT/JP2015/070302.
(Continued)

*Primary Examiner* — Craig D Ricci
*Assistant Examiner* — Janet L Coppins
(74) *Attorney, Agent, or Firm* — Buchanan, Ingersoll & Rooney PC (57) ABSTRACT

A method of healing an external wound involves applying an external wound-healing agent to an external wound, or bringing the external wound-healing agent applied to a substrate into contact with an external wound, wherein the external wound-healing agent includes, as an active ingredient, at least one compound of a glycerol alkyl ester represented by defined Formula (I) or a diglycerol alkyl ester
(Continued)

represented by defined Formula (II). In a further embodiment, the method involves bringing a fiber aggregate or a film into contact with an external wound, wherein the fiber aggregate or the film each includes a thermoplastic resin and at least one compound of the glycerol alkyl ester or the diglycerol alkyl ester.

9 Claims, 6 Drawing Sheets

(51) Int. Cl.
  *A61K 9/00* (2006.01)
  *A61L 15/44* (2006.01)
  *A61K 9/70* (2006.01)
  *A61K 47/32* (2006.01)
(52) U.S. Cl.
  CPC ............... *A61L 15/44* (2013.01); *A61P 17/02* (2018.01); *A61L 2300/412* (2013.01)

(56) References Cited

U.S. PATENT DOCUMENTS

| | | |
|---|---|---|
| 2004/0241216 A1 | 12/2004 | Klun et al. |
| 2006/0127437 A1 | 6/2006 | Kennedy et al. |
| 2007/0053957 A1 | 3/2007 | Kennedy et al. |
| 2007/0059350 A1 | 3/2007 | Kennedy et al. |
| 2008/0249453 A1 | 10/2008 | Effing |
| 2008/0249485 A1 | 10/2008 | Effing |
| 2008/0249486 A1 | 10/2008 | Effing |
| 2011/0117176 A1 | 5/2011 | Klun et al. |
| 2012/0316517 A1* | 12/2012 | Croizat ............ A61F 13/00063 604/304 |

FOREIGN PATENT DOCUMENTS

| | | |
|---|---|---|
| EP | 1304115 A1 | 4/2003 |
| EP | 2902102 A1 | 8/2015 |
| GB | 720116 A | 12/1954 |
| JP | 02-216265 A | 8/1990 |
| JP | 2003-500556 A | 1/2003 |
| JP | 2006-248908 A | 9/2006 |
| JP | 2008-523149 A | 7/2008 |
| JP | 2009-519916 A | 5/2009 |
| JP | 2009-173641 A | 8/2009 |
| KR | 10-2007-0100733 A | 10/2007 |
| WO | WO 00/71789 A1 | 11/2000 |
| WO | WO 2006/065800 A2 | 6/2006 |

OTHER PUBLICATIONS

Written Opinion (PCT/ISA/237) dated Sep. 15, 2015, by the Japan Patent Office as the International Searching Authority for International Application No. PCT/JP2015/070302.
Office Action issued by the Korean Patent Office in corresponding Korean Patent Application No. 2017-7001807 dated Sep. 22, 2017.
Niazi: "Handbook of Pharmaceutical Manufacturing Formulations Semisolid Products vol. 4", CRC Press, Retrieved from the Internet, Jan. 1, 2004, p. 123: example Burn creams, XP-055238511.
Internet Citation: "Burn relief", Retrieved from the Internet, Feb. 13, 2004. page 2: examples First Aid/burn cream, XP-002332368.
Anonymous Ed—Solvay: "Polyglycerols in Personal Care (Application Data Sheet)", Internet Citation, Jan. 1, 2008, pp. 1-11, XP-002699276.
Database WPI: Week 201531, Thomson Specific, London, GB, AN 2015-18967U, XP-002777825.
Extended Search Report issued by the European Patent Office in corresponding European Patent Application No. 15822287.7-1114 dated Feb. 9, 2018.

* cited by examiner

Day 0 Animal No.201

Fig.3

Day 3 Animal No.103

Fig.4

Day 6 Animal No. 201

Fig.5

Day 9 Animal No. 303

Fig. 6

EXTERNAL WOUND-HEALING AGENT, AND EXTERNAL WOUND-HEALING MATERIAL

RELATED APPLICATIONS

This application is a divisional of U.S. application Ser. No. 15/326,150, filed on Jan. 13, 2017, which is a U.S. National Stage of International Application No. PCT/JP2015/070302, filed on Jul. 15, 2015, which in turn claims priority to Japanese Application No. 2014-145189, filed on Jul. 15, 2014, the entire contents of each of which is incorporated herein by reference.

TECHNICAL FIELD

The present invention relates to an external wound-healing agent and an external wound-healing material.

BACKGROUND ART

A cloth-like product is conventionally known which is made of polyolefin fibers, has water permeability, and in which a polyglycerol fatty acid ester remains attached in an amount of from 0.05% to 1% by mass with respect to the cloth-like product (see, for example, Document 1).

A disinfectant composition is also known which contains from (A) to (C) components ((A), a lower alcohol; (B), (b1) an organic acid and an alkali metal salt thereof, and/or (b2) an inorganic acid and an alkali metal salt thereof; (C) at least one nonionic surfactant selected from a monoglycerol fatty acid ester, a polyglycerol fatty acid ester, a sorbitan fatty acid ester, a polyoxyethylene sorbitan fatty acid ester, or a sucrose fatty acid ester) at a predetermined ratio with respect to the total amount of the composition and contains (D) component (water), and the stock solution of which composition has a pH set to be within a range of from 8 to 12 at 25° C. (see, for example, Document 2).

The impregnation of a nonwoven fabric with a cosmetic oil having a viscosity at 25° C. in a range of from 50 to 1,000 mPa·s, the cosmetic oil containing a polyglycerol fatty acid ester, are known (see, for example, Document 3).

Document 1: Japanese Patent Application Laid-Open (JP-A) No. H02-216265
Document 2: Japanese Patent Application Laid-Open (JP-A) No. 2009-173641
Document 3: Japanese Patent Application Laid-Open (JP-A) No. 2006-248908

SUMMARY OF INVENTION

Technical Problem

However, it is unknown that a certain glycerol alkyl ester or diglycerol alkyl ester can be an active ingredient for healing an external wound.

An object of the invention is to provide an external wound-healing agent and an external wound-healing material, each having a therapeutic effect on an external wound.

Solution to Problem

Specific methods for solving the above problem is as described below.

(1) An external wound-healing agent comprising, as an active ingredient, at least one compound of a glycerol alkyl ester or a diglycerol alkyl ester, the glycerol alkyl ester represented by the following Formula (I):

wherein, in Formula (I), each of $R^1$, $R^2$, and $R^3$ independently represents a hydrogen atom or an acyl group having from 12 to 22 carbon atoms, and at least one of $R^1$, $R^2$, or $R^3$ is an acyl group having from 12 to 22 carbon atoms, the diglycerol alkyl ester represented by the following Formula (II):

wherein, in Formula (II), each of $R^4$, $R^5$, $R^6$, and $R^7$ independently represents a hydrogen atom or an acyl group having from 12 to 22 carbon atoms, and at least one of $R^4$, $R^5$, $R^6$, or $R^7$ is an acyl group having from 12 to 22 carbon atoms.

(2) The external wound-healing agent according to (1), wherein the glycerol alkyl ester is at least one of glycerol palmitate or glycerol stearate, and the diglycerol alkyl ester is at least one of diglycerol palmitate or diglycerol stearate.

(3) An external wound-healing material comprising:

a fiber aggregate; or a film, the fiber aggregate or the film each comprising:

a thermoplastic resin; and at least one compound of a glycerol alkyl ester or a diglycerol alkyl ester, the glycerol alkyl ester being represented by the following Formula (I):

wherein, in Formula (I), each of $R^1$, $R^2$, and $R^3$ independently represents a hydrogen atom or an acyl group having from 12 to 22 carbon atoms, and at least one of $R^1$, $R^2$, or $R^3$ is an acyl group having from 12 to 22 carbon atoms, the diglycerol alkyl ester being represented by the following Formula (II):

wherein, in Formula (II), each of $R^4$, $R^5$, $R^6$, and $R^7$ independently represents a hydrogen atom or an acyl group having from 12 to 22 carbon atoms, and at least one of $R^4$, $R^5$, $R^6$, or $R^7$ is an acyl group having from 12 to 22 carbon atoms.

(4) The external wound-healing material according to (3), wherein the glycerol alkyl ester is at least one of glycerol palmitate or glycerol stearate, and the diglycerol alkyl ester is at least one of diglycerol palmitate or diglycerol stearate.

(5) The external wound-healing material according to (3) or (4), wherein the thermoplastic resin is at least one resin selected from the group consisting of olefin resins, urethane resins, amide resins, ester resins, acrylic resins, styrene resins, and carbonate resins.

(6) The external wound-healing material according to (5), wherein the thermoplastic resin is an olefin resin.

(7) The external wound-healing material according to (5) or (6), wherein the olefin resin is at least one of an ethylene copolymer or a propylene copolymer.

(8) The external wound-healing material according to any one of (3) to (7), wherein the fiber aggregate is a nonwoven fabric.

Advantageous Effects of Invention

According to the invention, an external wound-healing agent and an external wound-healing material, each having a therapeutic effect on an external wound, can be provided.

DESCRIPTION OF EMBODIMENTS

Every numerical range expressed using "from . . . to . . . " throughout this specification means a range including the numerical values before and after "to" as a lower limit and an upper limit.

Specific embodiments of the invention will be described below in detail. The invention, however, is not limited to the following embodiments, and modifications can be made as appropriate without departing from the spirit of the invention.

External Wound-Healing Agent

An external wound-healing agent according to one embodiment includes, as an active ingredient, at least one compound of a glycerol alkyl ester represented by the following Formula (I) or a diglycerol alkyl ester represented by the following Formula (II).

In Formula (I), each of $R^1$, $R^2$, and $R^3$ independently represents a hydrogen atom or an acyl group having from 12 to 22 carbon atoms, and at least one of $R^1$, $R^2$, or $R^3$ is an acyl group having from 12 to 22 carbon atoms. In Formula (II), each of $R^4$, $R^5$, $R^6$, and $R^7$ independently represents a hydrogen atom or an acyl group having from 12 to 22 carbon atoms, and at least one of $R^4$, $R^5$, $R^6$, or $R^7$ is an acyl group having from 12 to 22 carbon atoms.

The external wound-healing agent according to this embodiment, by virtue of including, as an active ingredient, at least one compound of a glycerol alkyl ester or a diglycerol alkyl ester having a predetermined chemical structure, has a therapeutic effect on an injury (wound) of a body tissue, such as skin, caused by a physical or chemical external factor (external cause).

Examples of external wounds include wounds due to physical factors and external wounds due to chemical factors. Examples of external wounds due to physical factors include injuries due to external mechanical force, burn injuries (burns) due to heat, infrared radiation, and ultraviolet radiation, and electrical injuries due to currents. Examples of external wounds due to chemical factors include injuries of skin and other tissues due to acids, alkalis, bacteria, microorganisms, and other factors.

For example, by applying the external wound-healing agent to these external wounds or bringing the external wound-healing agent applied (attached) to a substrate into contact with the external wounds, a therapeutic effect on the external wounds can be obtained.

A description will now be given of ingredients in the external wound-healing agent.

Glycerol Alkyl Ester

The glycerol alkyl ester for use in this embodiment is a compound represented by the following Formula (I).

In Formula (I), each of $R^1$, $R^2$, and $R^3$ independently represents a hydrogen atom or an acyl group having from 12 to 22 carbon atoms. At least one of $R^1$, $R^2$, or $R^3$ is an acyl group having from 12 to 22 carbon atoms.

In particular, in Formula (I), each of $R^1$, $R^2$, and $R^3$ is independently more preferably a hydrogen atom or an acyl group having from 12 to 20 carbon atoms, still more preferably a hydrogen atom or an acyl group having from 16 to 18 carbon atoms.

Examples of the structure of the acyl group of $R^1$ to $R^3$ include $C_{11}H_{23}CO-$, $C_{13}H_{27}CO-$, $C_{15}H_{31}CO-$, $C_{17}H_{35}CO-$, and $C_{19}H_{39}CO-$. Of these, $C_{15}H_{31}CO-$ and $C_{17}H_{35}CO-$ are preferred.

Examples of the glycerol alkyl ester for use in the invention include glycerol palmitate and glycerol stearate, and, in particular, glycerol stearate is preferred.

The glycerol alkyl ester may be a monoester, a diester, or a triester, and is preferably a monoester. The monoester is more preferably glycerol monostearate, for example.

Diglycerol Alkyl Ester

The diglycerol alkyl ester for use in the invention is a compound represented by the following Formula (II).

In Formula (II), each of $R^4$, $R^5$, $R^6$, and $R^7$ is independently a hydrogen atom or an acyl group having from 12 to 22 carbon atoms. At least one of $R^4$, $R^5$, $R^6$, or $R^7$ is an acyl group having from 12 to 22 carbon atoms.

In particular, in Formula (II), each of $R^4$, $R^5$, $R^6$, and $R^7$ is independently more preferably a hydrogen atom or an acyl group having from 12 to 20 carbon atoms, still more preferably a hydrogen atom or an acyl group having from 16 to 18 carbon atoms.

Examples of the diglycerol alkyl ester for use in the invention include diglycerol palmitate and diglycerol stearate, and, in particular, diglycerol stearate is preferred.

The diglycerol alkyl ester may be a monoester, a diester, a triester, or a tetraester, and is preferably a monoester. The monoester is more preferably diglycerol monostearate, for example.

The amount of the at least one compound of the glycerol alkyl ester represented by the above Formula (I) or the diglycerol alkyl ester represented by the above Formula (II) is not particularly limited as long as an amount necessary for producing a therapeutic effect on an external wound is contained in the external wound-healing agent, and is preferably from 0.05 part by mass to 5 parts by mass, more preferably from 0.1 part by mass to 4 parts by mass, still more preferably from 0.5 part by mass to 3 parts by mass, with respect to 100 parts by mass of the external wound-healing agent.

Other Ingredients

The external wound-healing agent may contain other conventionally known ingredients, as necessary, to the extent that the object of the invention is not adversely affected. Examples of the other ingredients include oily ingredients, such as hydrocarbon oils, ester oils, higher fatty acids, silicone oils, and fluorine oils, organic acids, alkali metal salts of organic acids, inorganic acids, alkali metal salts of inorganic acids, surfactants, UV absorbers, skin irritation reducing agents, water-soluble solvents, dyes, perfumes, antiseptics, bactericides, humectants, and skin astringents.

External Wound-Healing Material

A description will now be given of one embodiment of the external wound-healing material according to the invention. The external wound-healing agent according to one embodiment has a fiber aggregate including a thermoplastic resin and at least one compound of a glycerol alkyl ester represented by the following Formula (I) and a diglycerol alkyl ester represented by the following Formula (II).

In Formula (I), each of $R^1$, $R^2$, and $R^3$ independently represents a hydrogen atom or an acyl group having from 12 to 22 carbon atoms, and at least one of $R^1$, $R^2$, or $R^3$ is an acyl group having from 12 to 22 carbon atoms. In Formula (II), each of $R^4$, $R^5$, $R^6$, and $R^7$ independently represents a hydrogen atom or an acyl group having from 12 to 22 carbon atoms, and at least one of $R^4$, $R^5$, $R^6$, or $R^7$ is an acyl group having from 12 to 22 carbon atoms.

The external wound-healing material according to this embodiment, by virtue of having a fiber aggregate including at least one compound of a glycerol alkyl ester or a diglycerol alkyl ester having a predetermined chemical structure, has a therapeutic effect on the external wounds described above. By bringing the fiber aggregate including at least one of these compounds into contact with external wounds described above, a therapeutic effect on the external wounds can be obtained over a long period of time.

The glycerol alkyl ester represented by the above Formula (I) and the diglycerol alkyl ester represented by the above Formula (II) are the same as the glycerol alkyl ester and the diglycerol alkyl ester in the external wound-healing agent described above, and thus the description thereof will be omitted.

Examples of the external wound-healing material include, but are not limited to, sanitary supplies, medical supplies, and raw materials thereof. The external wound-healing material may be used in any manner as long as the external wound-healing material can be in contact with an external wound site. For example, the external wound-healing material may be used in such a manner that the external wound-healing material is provided with stickiness or adhesiveness and stuck directly to an external wound site. Alternatively, the external wound-healing material may be used in such a manner that the external wound-healing material is stuck to a part of a substrate having stickiness or adhesiveness, and the face to which the external wound-healing material is stuck is applied to skin.

More specific examples of the external wound-healing material include sheets, mattress materials for beds, covers (covers of futons, pillows, and others), bed pads, undershirts/T-shirts, patient gowns, examination gowns, and underpants for use to prevent bedsore or ameliorate symptoms of bedsores; gloves, socks, and bandages for use to prevent incised wounds, such as chaps, or ameliorate symptoms of incised wounds; and gum fillers and root canal fillers for use in the oral cavity.

Examples of the fiber aggregate for use in this embodiment include nonwoven fabrics, woven fabrics, knitted fabrics, solid waddings, fiber sheets in sheet form such as paper, plied yarns, braids, and ropes, and nonwoven fabrics are particularly preferred. Examples of nonwoven fabrics include various nonwoven fabrics such as spunbond nonwoven fabrics, spunlaced nonwoven fabrics, and meltblown nonwoven fabrics.

These nonwoven fabrics are produced by various known methods, for example, wet methods (papermaking system), dry methods (airlaying system, carding system), meltblowing, or spunbonding. To the extent that the object of the invention is not adversely affected, additives commonly used in papermaking, such as dispersants, mucilages, and paper strengthening agents, may be added, as necessary. The fibers of the nonwoven fabrics may have round, polygonal, modified, and various other known cross-sectional shapes.

The nonwoven fabric for use in this embodiment may be monocomponent fibers or conjugate fibers selected from core-sheath fibers, splittable fibers, or sea-island fibers. In this case, at least one of the glycerol alkyl ester represented by the above Formula (I) or the diglycerol alkyl ester represented by the above Formula (II) for use in this embodiment may be contained throughout the conjugate fibers or in part of the resin constituting the conjugate fibers.

In the nonwoven fabric for use in this embodiment, two or more fibers may be mixed. In the case of mixed fibers, at least one of the glycerol alkyl ester represented by the above Formula (I) or the diglycerol alkyl ester represented by the above Formula (II) for use in this embodiment may be contained throughout the two or more fibers or only in part of the fibers.

Thermoplastic Resin

"Thermoplastic resins" as used herein include not only what are generally referred to as thermoplastic resins, which are high molecular compounds that soften and become flowable with increasing temperature and, when cooled, become relatively hard and strong but has no rubber-like elasticity, but also thermoplastic elastomers, which are high molecular compounds that are made of a copolymer of a polymer that forms a hard segment that is crystalline and has a high melting point or a hard segment having high cohesion and a polymer that forms a soft segment that is amorphous and has a low glass transition temperature, and soften and become flowable with increasing temperature and, when cooled, become relatively hard and strong and has rubber-like elasticity.

Examples of thermoplastic resins include at least one resin selected from the group consisting of olefin resins, urethane resins, amide resins, ester resins, acrylic resins, styrene resins, and carbonate resins. These thermoplastic resins may be used singly, or in mixture of two or more kinds thereof.

Among these thermoplastic resins, olefin resins are particularly preferred. Olefin resins, which have favorable biocompatibility, are suitable for use in next-to-skin applications.

Urethane resins, which have moisture permeability, are suitable for use in external wound-healing agent applications.

Olefin resins, urethane resins, and amide resins, which are soft elastomeric resins, advantageously conform to irregular faces of contact objects.

Carbonate resins, which are usable in wide temperature ranges and have high light resistance, can advantageously be used over a long period of time.

The olefin resin for use is not particularly limited and may be one which is conventionally known. "Olefin resin" as used herein means a homopolymer of an olefin, a copolymer of two or more olefins, a polymer blend or a polymer alloy of two or more olefins, or a copolymer of an olefin and any other monomer.

The olefin resin is preferably at least one of an ethylene copolymer or a propylene copolymer.

Examples of the olefin resin include ethylene polymers such as low-density polyethylene, ultra low-density polyethylene, linear low-density polyethylene, medium-density polyethylene, and high-density polyethylene. Further examples of the olefin resin include ethylene polymers such as copolymers of ethylene and a vinyl compound, such as an α-olefin having from 3 to 12 carbon atoms, styrene, vinyl acetate, (meth)acrylic acid, (meth)acrylic acid ester, or an ionomer.

Examples of the α-olefin having from 3 to 12 carbon atoms include, but are not limited to, propylene, 1-butene, 1-pentene, 3-methyl-1-butene, 4-methyl-1-pentene, 1-hexene, 1-octene, 1-decene, and 1-dodecene.

Further examples of the olefin resin include propylene homopolymers and propylene copolymers. Examples of propylene copolymers include propylene/ethylene block copolymers, propylene/ethylene random copolymers, propylene/ethylene/butylene block copolymers, and propylene/ethylene/butylene random copolymers.

Other examples of the olefin resin include α-olefin polymers having 4 or more carbon atoms, such as polybutene and polymethylpentene, and cyclic olefin copolymers, but are not limited thereto.

Examples of commercially available products of the olefin resin include "TAFMER (registered trademark)" series (e.g., A4085S, XM-7070, and A20085) available from Mitsui Chemicals, Inc.

The olefin resin is preferably an olefin elastomer from the viewpoint of elasticity and conformability to contact objects.

Examples of the olefin elastomer include those in which at least a polyolefin forms a hard segment that is crystalline and has a high melting point, and another polymer (e.g., a polyolefin, another polyolefin, or a polyvinyl compound) forms a soft segment that is amorphous and has a low glass transition temperature.

Examples of the polyolefin that forms a hard segment include polyethylene, polypropylene, and polybutene, but are not limited thereto.

Examples of commercially available products of the olefin elastomer include "NOTIO (registered trademark)" series (e.g., PN 3560 and PN 2060) available from Mitsui Chemicals, Inc.

The urethane resin for use is not particularly limited and may be one which is conventionally known. Urethane resins are basically synthesized by the addition polymerization reaction of a polyol compound and a polyisocyanate compound. The polyol compound and the polyisocyanate compound for use may be those described in WO 2009/051114.

Examples of the polyol compound include polyhydric alcohols, such as ethylene glycol, propylene glycol, tetramethylene glycol, and glycerol; polyether polyols, such as diethylene glycol, polyethylene glycol, dipropylene glycol, and polypropylene glycol; and polyester polyols.

Examples of the polyisocyanate compound include, but are not limited to, aromatic isocyanates, such as tolylene diisocyanate and diphenylmethane diisocyanate, and aliphatic isocyanates, such as trimethylene diisocyanate, hexamethylene diisocyanate, and ethylene diisocyanate.

The amide resin for use is not particularly limited and may be one which is conventionally known. The amide resin can be obtained, for example, by the polycondensation of a diamine compound and a dicarboxylic acid compound, the polycondensation of an aminocarboxylic acid compound, or the ring-opening polymerization of a lactam. Specific examples of the amide resin include 6-nylon and 6,6-nylon.

Examples of the diamine compound include ethylenediamine, 1,2-propanediamine, hexamethylenediamine, octamethylenediamine, o-phenylenediamine, m-phenylenediamine, p-phenylenediamine, piperazine, 2,5-dimethylpiperazine, 4,4'-diaminophenyl ether, and xylylenediamine.

Examples of the dicarboxylic acid compound include oxalic acid, malonic acid, succinic acid, adipic acid, acetonedicarboxylic acid, sebacic acid, fumaric acid, maleic acid, itaconic acid, citraconic acid, phthalic acid, isophthalic acid, terephthalic acid, 2-butyl terephthalic acid, tetrachloroterephthalic acid, acetylenedicarboxylic acid, 1,2-cyclohexanedicarboxylic acid, 1,4-cyclohexanedicarboxylic acid, and ω-poly(ethyleneoxy)dicarboxylic acid.

Examples of the aminocarboxylic acid compound include glycine, alanine, phenylalanine, ω-aminohexanoic acid, ω-aminodecanoic acid, and ω-aminoundecanoic acid.

Examples of the lactam include ω-caprolactam, azetidinone, and pyrrolidone, but are not limited thereto.

Examples of the amide resin also include polyamide elastomers.

"Polyamide elastomer" as used herein refers to compounds made of a copolymer of a polymer that forms a hard segment that is crystalline and has a high melting point and a polymer that forms a soft segment that is amorphous and has a low glass transition temperature, the polymer that forms a hard segment having an amide bond (—CONH—) in its main chain.

Examples of the polyamide elastomer include those in which at least a polyamide forms a hard segment that is crystalline and has a high melting point, and another polymer (e.g., polyester or polyether) forms a soft segment that is amorphous and has a low glass transition temperature. Specific examples of the polyamide elastomer include thermoplastic amide elastomers (TPA) prescribed in JIS K6418: 2007, but are not limited thereto.

The ester resin for use is not particularly limited and may be one which is conventionally known.

Examples of the ester resin include polyethylene terephthalate, polyethylene isophthalate, polybutylene terephthalate, polyethylene naphthalate, polybutylene naphthalate, and polylactic acid, but are not limited thereto. Of these, polyethylene terephthalate is preferred.

The acrylic resin for use is not particularly limited and may be one which is conventionally known.

Examples of the acrylic resin include homopolymers and copolymers of monomers of acrylic acid, acrylic acid esters, methacrylic acid, and methacrylic acid esters, such as acrylic acid, methyl acrylate, ethyl acrylate, n-butyl acrylate, t-butyl acrylate, 2-ethylhexyl acrylate, 2-dimethylaminoethyl acrylate, 2-hydroxyethyl acrylate, methacrylic acid, methyl methacrylate, ethyl methacrylate, n-butyl methacrylate, t-butyl methacrylate, 2-ethylhexyl methacrylate, 2-dimethylaminoethyl methacrylate, and 2-hydroxyethyl methacrylate, but are not limited thereto.

The styrene resin for use is not particularly limited and may be one which is conventionally known.

Examples of the styrene resin include polystyrene and poly(α-methylstyrene), but are not limited thereto.

Examples of the styrene resin also include polystyrene elastomers. Examples of the polystyrene elastomer include those in which at least polystyrene forms a hard segment, and another polymer (e.g., polybutadiene, polyisoprene, polyethylene, hydrogenated polybutadiene, or hydrogenated polyisoprene) forms a soft segment that is amorphous and has a low glass transition temperature, but are not limited thereto.

Specific examples of the polystyrene elastomer include styrene-butadiene copolymers [SB (polystyrene-polybutadiene), SBS (polystyrene-poly(butylene) block-polystyrene), SEBS (polystyrene-poly(ethylene/butylene) block-polystyrene)], styrene-isoprene copolymers [SIS (polystyrene-polyisoprene block-polystyrene)], and styrene-propylene copolymers [SEP (polystyrene-(ethylene/propylene) block), SEPS (polystyrene-poly(ethylene/propylene) block-polystyrene), SEEPS (polystyrene-poly(ethylene-ethylene/propylene) block-polystyrene), SEB (polystyrene(ethylene/butylene) block)], but are not limited thereto.

Examples of commercially available products of the polystyrene elastomer include "Tuftec" series (e.g., H1041, H1043, H1051, H1052, H1053, and H1062) available from Asahi Kasei Corporation.

The carbonate resin for use is not particularly limited and may be one which is conventionally known.

Examples of the carbonate resin include bis(4-hydroxyphenyl) methane, 1,1-bis(4-hydroxyphenyl) ethane, 2,2-bis(4-hydroxyphenyl) propane, and 2,2-bis(4-hydroxyphenyl) butane, but are not limited thereto.

The amount of the at least one compound of the glycerol alkyl ester represented by the above Formula (I) or the diglycerol alkyl ester represented by the above Formula (II) is not particularly limited as long as the at least one compound is contained in the fiber aggregate in an amount necessary to produce a therapeutic effect on an external wound, and is preferably from 0.05 part by mass to 5 parts by mass, more preferably from 0.1 part by mass to 4 parts by mass, still more preferably from 0.5 part by mass to 3 parts by mass, with respect to 100 parts by mass of the thermoplastic resin.

The fiber aggregate may contain other conventionally known ingredients, as necessary, to the extent that the object of the invention is not adversely affected. The other ingredients are the same as those which may be contained in the external wound-healing agent described above.

The external wound-healing material according to this embodiment includes, in the fibers forming the fiber aggregate, a thermoplastic resin and at least one of the glycerol alkyl ester represented by Formula (I) or the diglycerol alkyl ester represented by Formula (II). This configuration allows the active ingredients to be retained without flowing down during use, leading to a high external wound-healing effect, unlike configurations in which a compound such as glycerol alkyl ester is attached to a fiber surface by application or other methods.

To produce such fibers, known methods can be used. Specifically, in producing fibers or a nonwoven fabric, thermoplastic resin pellets are spun with the glycerol alkyl ester and/or the other compound added. Using the thermoplastic resin pellets containing the glycerol alkyl ester and/or the other compound at a high concentration, what is called a masterbatch, advantageously enables more uniform mixing.

Another Embodiment

An external wound-healing material according to another embodiment can be an external wound-healing material having a resin sheet (film) including a thermoplastic resin and at least one compound of the glycerol alkyl ester represented by the above Formula (I) or the diglycerol alkyl ester represented by the above Formula (II).

Fine irregularities can be formed on the surface of the external wound-healing material to impart a function to the external wound-healing material. For example, fine projections can be formed on the surface of the resin sheet to provide the external wound-healing material with stickiness or adhesiveness.

Examples of sticky sheets having stickiness and adhesive sheets having adhesiveness include those described in U.S. Pat. No. 8,153,254, U.S. Publication No. 2010/0080951, Japanese Patent Application Laid-Open (JP-A) No. 2008-201883, and U.S. Publication No. 2011/0271497.

One example of the resin sheet on the surface of which fine projections are formed is a resin sheet including a substrate and a plurality of columnar projections formed on the surface of the substrate, wherein the columnar projections have heights from 100 nm to 200 μm, the number of the columnar projections per unit projected area of at least part of the surface of the substrate being from $10^4/cm^2$ to $10^{10}/cm^2$, wherein the ratio of the total area of the tops of this number of columnar projections to the unit projected area of the surface of the substrate on which this number of columnar projections are formed is from $1\times10^{-10}$ to $1-1\times10^{-10}$, wherein at least the resin contained in the substrate and the projections is a thermoplastic resin, and wherein the thermoplastic resin has a tackiness at 25° C., as determined by the probe tack test method, of 25 N/cm² or less. The thermoplastic resin may be any of the resins described above.

The thermoplastic resin has a tackiness at 25° C., as determined by the probe tack test method, of 25 N/cm² or less, preferably 20 N/cm² or less, more preferably 15 N/cm² or less.

In a case in which the tackiness at 25° C. of the thermoplastic resin is too high, a molded product is difficult to release from a mold in molding, leading to low efficiency of resin-sheet molding. In addition, molded columnar projections tend to come close to each other and stick together, leading to a resin sheet with low shape retention.

In a case in which the tackiness at 25° C. of the thermoplastic resin is 25 N/cm² or less, a molded product is easy to release from a mold in molding, leading to high efficiency of resin-sheet molding. In addition, molded columnar projections are less likely to come close to each other and stick together, leading to a resin sheet with high shape retention.

The tackiness at 25° C. of the thermoplastic resin is preferably at least about 0.01 N/cm².

In a case in which the tackiness at 25° C. of the thermoplastic resin is too low, it is difficult to bond and form a member (e.g., a support) of a different material (a resin different from the resin contained in the substrate and the projections) onto the face of the resin sheet opposite to the face on which the columnar projections are formed.

In a case in which the tackiness at 25° C. of the thermoplastic resin is 0.01 N/cm² or more, problems with the adhesion to the member of a different material are less likely to occur.

The tackiness at 25° C. of the thermoplastic resin is determined using a tackiness tester (TAC-II available from RHESCA CO., LTD.) under the following measurement conditions. At room temperature (25° C.), a cylindrical stainless-steel probe having a diameter of 5 mm is brought into contact with the surface of a sheet made of the thermoplastic resin at a rate of 120 mm/min, and a load of 200 N/cm² is applied for 1 second, after which the probe is peeled off in the vertical direction at a rate of 120 mm/min. The value of resistance (load) against the probe caused by stickiness during the peeling is measured to determine the tackiness at 25° C.

The thermoplastic resin preferably has a storage modulus E' at 25° C. of from 1 MPa to 5 GPa, more preferably from 1 MPa to 1 GPa, still more preferably from 4 MPa to 500 MPa.

In a case in which the storage modulus E' at 25° C. of the thermoplastic resin is too high, a resin sheet, when brought into contact with an irregular face, tends to exhibit poor conformability and peel off the face. In a case in which the storage modulus E' at 25° C. of the thermoplastic resin is too low, the columnar projections tend to come close to each other and stick together, leading to a resin sheet with low shape retention.

In a case in which the storage modulus E' at 25° C. of the thermoplastic resin is within the above range, the columnar projections are less likely to come close to each other and stick together, leading to a resin sheet with higher shape retention.

The storage modulus E' at 25° C. of the thermoplastic resin is determined using a solid viscoelasticity analyzer (RSA-III available from TA Instruments Japan Inc.) under the following measurement conditions. A sheet made of the thermoplastic resin is cut into a strip 3 mm wide×5 cm long. The strip is placed in a fixture at a chuck distance of 20 mm. In a nitrogen environment, a storage modulus E' is measured in the tensile mode at a measurement frequency of 1 Hz while the temperature is raised from −50° C. to 100° C. at a rate of 3° C./min, thereby determining the storage modulus E' at 25° C.

The thermoplastic resin preferably has a softening point of from 40° C. to 300° C., more preferably from 50° C. to 300° C., still more preferably from 60° C. to 300° C.

In a case in which the softening point of the thermoplastic resin is too high, the resin may decompose during molding. In a case in which the temperature difference between the softening point of the thermoplastic resin and room temperature is too large, a heat cycle tends to require a long time, leading to low efficiency of resin-sheet production. In a case in which the softening point of the thermoplastic resin is too low, the resin tends to soften at room temperature during use to cause the projections to stick together, leading to a resin sheet with low shape retention.

In a case in which the softening point of the thermoplastic resin is within the above range, the resin has favorable flowability, thus enabling shapes as designed, and projections are formed in a short time, leading to higher efficiency of resin-sheet molding. In addition, a resin sheet having such higher shape retention is provided that the columnar projections are less likely to stick together during molding, storage, and use.

The softening point of the thermoplastic resin is determined using a thermomechanical analyzer (TMA-50 available from Shimadzu Corporation) under the following measurement conditions. A sheet made of the thermoplastic resin is cut to 5 mm wide×15 mm long to prepare a test piece. The test piece is heated from 10° C. to 250° C. at a rate of 5° C./min, and from the intersection of tangents to a thermo mechanical analysis (TMA) curve around a glass transition temperature, a TMA softening temperature (softening point) is determined.

The thermoplastic resin preferably has a breaking strength of from 1 MPa to 1,000 MPa, more preferably from 5 MPa to 500 MPa, still more preferably from 10 MPa to 100 MPa.

In a case in which the breaking strength of the thermoplastic resin is too high, the resin may be less easy to load into a mold, leading to low molding efficiency. In a case in which the breaking strength of the thermoplastic resin is too low, the columns may rupture when a resin sheet is peeled off a mold.

The breaking strength is determined in accordance with ASTM D638.

The columnar projections are preferably formed by thermal imprinting. Thermal imprinting, which allows fine die shapes to be accurately transferred to enable shapes as designed, provides excellent moldability.

A resin sheet according to a modification may have, on a face of the substrate on which columnar projections are not formed, a layer of a resin different from the resin contained in the substrate and the columnar projections. The resin sheet may have, on the face opposite to the face on which columnar projections are formed, a layer of a resin different from the resin contained in the substrate and the columnar projections.

Examples of the layer of a different resin include support layers, adhesive layers, and other layers.

The resin may be of any type different from that of the resin contained in the substrate and the columnar projections and can be selected according to the intended use of the resin sheet, as appropriate. The resin may be, but not necessarily, a thermoplastic resin.

The average thickness of the resin sheet is not particularly limited and can be selected according to, for example, the intended use of the resin sheet, as appropriate. The thickness of the resin sheet is preferably from 200 nm to 5 mm from the viewpoint of economic efficiency, molding efficiency, handleability after molding, and other factors.

In the resin sheet, the thickness of the substrate is preferably from 100 nm to 5 mm, more preferably from 1 μm to 5 mm, still more preferably from 10 μm to 5 mm, from the viewpoint of molding efficiency, handleability after molding, and other factors.

Method of Producing Resin Sheet

The resin sheet may be produced by any method, and any known method can be used, as appropriate. For example, the resin sheet can be, but not necessarily, produced by the following method.

The method of producing the resin sheet includes the steps of heating a thermoplastic resin substrate to a temperature higher than or equal to the softening point of the thermoplastic resin, pressing a die onto the heated thermoplastic resin substrate and then cooling the thermoplastic resin substrate to a temperature lower than or equal to the softening point of the thermoplastic resin, and separating the die from the cooled thermoplastic resin substrate to form columnar projections.

This process is a process of a molding method what is called thermal imprinting.

According to the method of producing the resin sheet, even projections of fine structure can be accurately formed as designed. This method of producing the resin sheet requires a shorter time for forming projections than injection molding, in which a liquid resin is injected into a mold.

EXAMPLES

The invention will now be described in more detail with reference to Examples, but these Examples are not intended to limit the invention.

Production of Nonwoven Fabric

A composition including an olefin resin and a glycerol alkyl ester compound represented by the above Formula (I) was prepared as described below. The olefin resin used was a propylene polymer (PP-1) having a melting point (Tm) of 163° C. and an MFR of 60 g/10 min. The glycerol alkyl ester used was POEM V-100 (trade name) glycerol stearate available from Riken Vitamin Co., Ltd. One part by mass of the glycerol alkyl ester was added to 99 parts by mass of the propylene polymer (PP-1) and mixed to prepare a propylene polymer composition (composition 1).

The composition 1 was melt spun by spunbonding to produce a long-fiber nonwoven fabric (nonwoven fabric B) having a basis weight of 20 g/m².

Using the nonwoven fabric B thus obtained and a nonwoven fabric A, which was obtained in the same manner as the nonwoven fabric B except that no glycerol alkyl ester was added, the healing effect was evaluated by the animal testing described below.

Animal Experiment

In this animal testing, the nonwoven fabric A or the nonwoven fabric B was applied to a burn injury site on the back of a rat, and the healing effects by the application of the nonwoven fabric A and B were evaluated. The details of the experiment will be described below.

The back of a rat was depilated. In the depilated portion, hot water at 80° C. was brought into contact for 5 seconds to form two burn injury sites. To the burn injury sites, the nonwoven fabric A (about 2 cm×2 cm) and the nonwoven fabric B (about 2 cm×2 cm) were applied, and occlusive patching was performed using non-permeable surgical tape (Blenderm, 3M) and adhesive flexible bandage (Silkytex 3, ALCARE Co., Ltd). On days 3, 6, and 9 after the application of the nonwoven fabrics A and B, the nonwoven fabrics were removed, and the healing effect was evaluated. Photographs were taken when the nonwoven fabrics were removed.

Test Group Configuration

Two burn injury sites were each formed on 15 rats, and then the nonwoven fabric A and the nonwoven fabric B were applied to each two burn injury sites. The 15 rats were divided into test groups A, B, and C each including 5 rats. On day 3, the nonwoven fabrics A and B on the rats of test group A were removed, and the skin conditions were assessed. On day 6, the nonwoven fabrics A and B on the rats of test group B were removed, and the skin conditions were assessed, and on day 9, the nonwoven fabrics A and B on the rats of test group C were removed, and the skin conditions were assessed.

Test group A: percutaneous administration (route of administration), animal No. 101-105, 5 males Test group B: percutaneous administration (route of administration), animal No. 201-205, 5 males Test group C: percutaneous administration (route of administration), animal No. 301-305, 5 males Weighing and Observation on General Condition The animals were weighed at the time of arrival, on the day following the arrival, at the end of quarantine, and at the start of testing. General conditions were observed every day.

Grouping

The animals, after being quarantined and going through an acclimation period, were confirmed to be healthy and have no abnormality in the skin and grouped by a randomized block design using grouping software (StatLight grouping 2001 (C) Yukms corp.) such that there was no imbalance in weight among the groups.

Evaluation Method

The skin conditions of the rats were evaluated according to the following scores (visual inspection).

0: asymptomatic, 1: slight, 2: mild, 3: moderate, 4: crusting, 5: necrosed

Method of Statistical Analysis

The test results were expressed as average values±standard errors and analyzed using EXSUS (Version 8.0, CAC EXICARE Corporation) and SAS (Version 9.3, SAS Institute Japan Ltd). For the scores of the skin conditions, the Wilcoxon test was conducted at a 2-sided significance level of 5%.

Effect on General Condition

The application of the nonwoven fabrics had no effect on general conditions.

Figure 1:
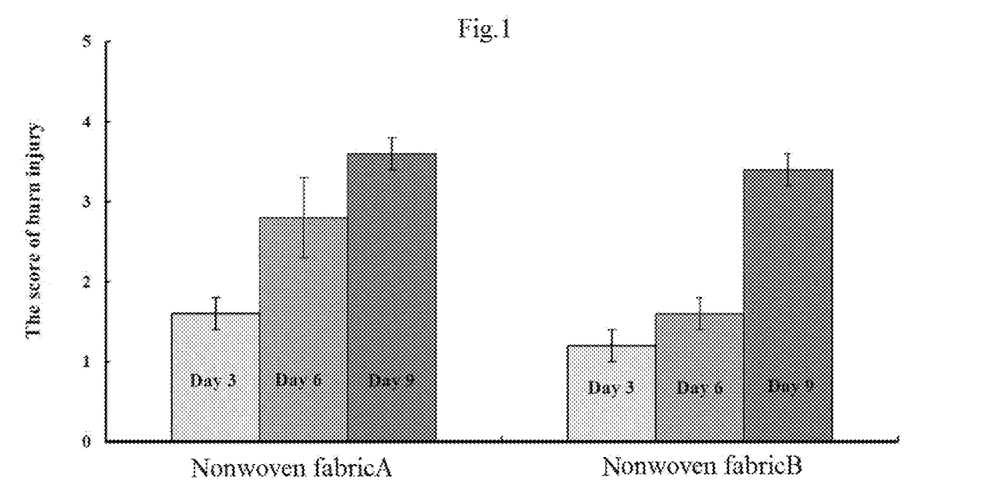
FIG. 1 is a graph showing scores of the skin conditions on day 3, day 6, and day 9 of burn injury sites to which nonwoven fabrics A and B were applied.
Figure 2:
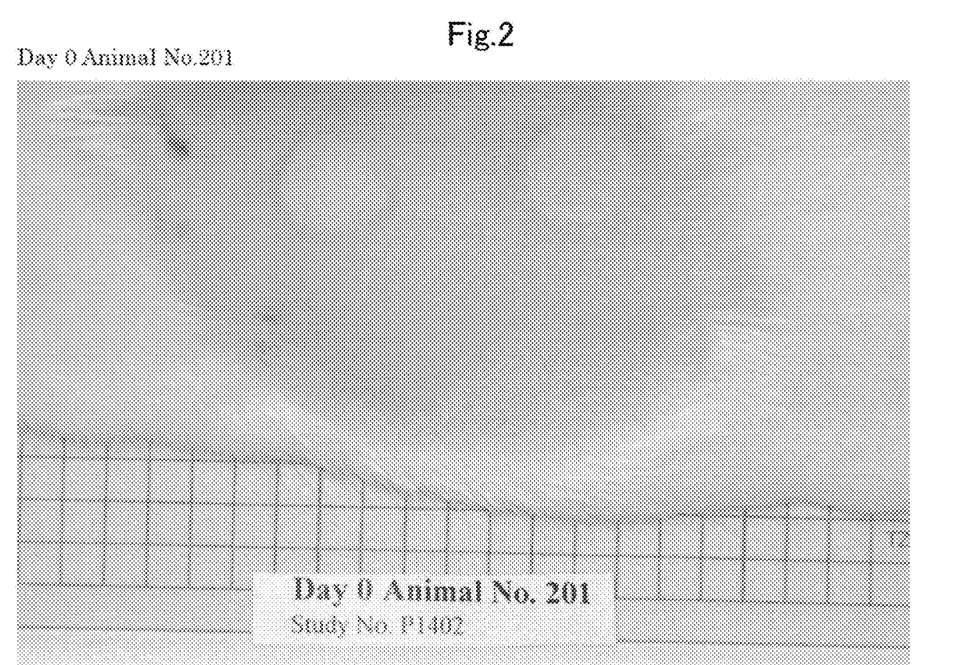
FIG. 2 is a photographic image showing the condition of a burn injury site on day 0 (immediately after the formation of the burn injury site)
Figure 3:
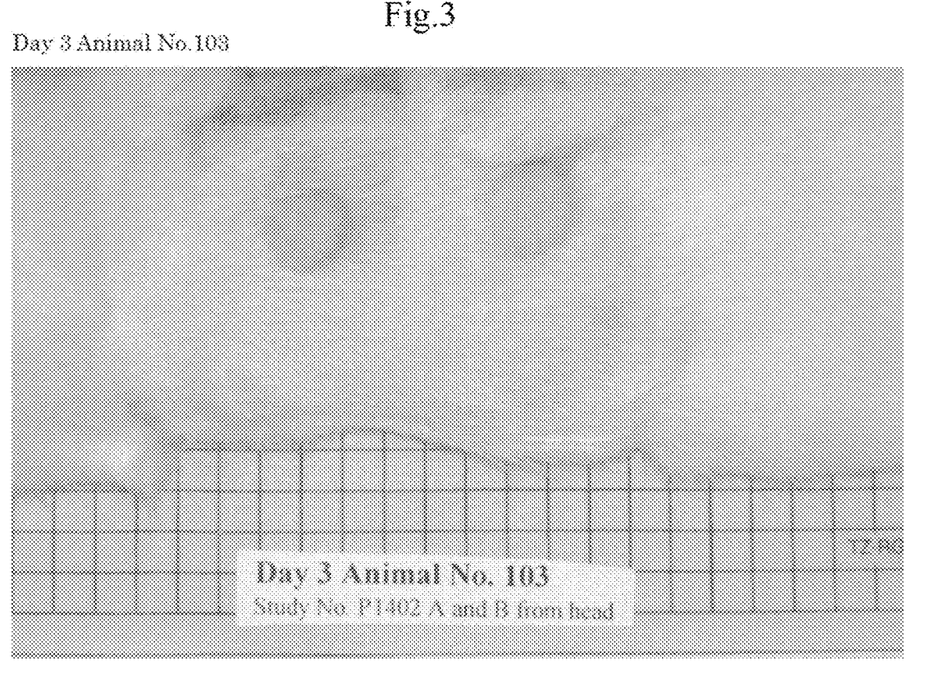
FIG. 3 is a photographic image showing the condition of a burn injury site on day 3.
Figure 4:
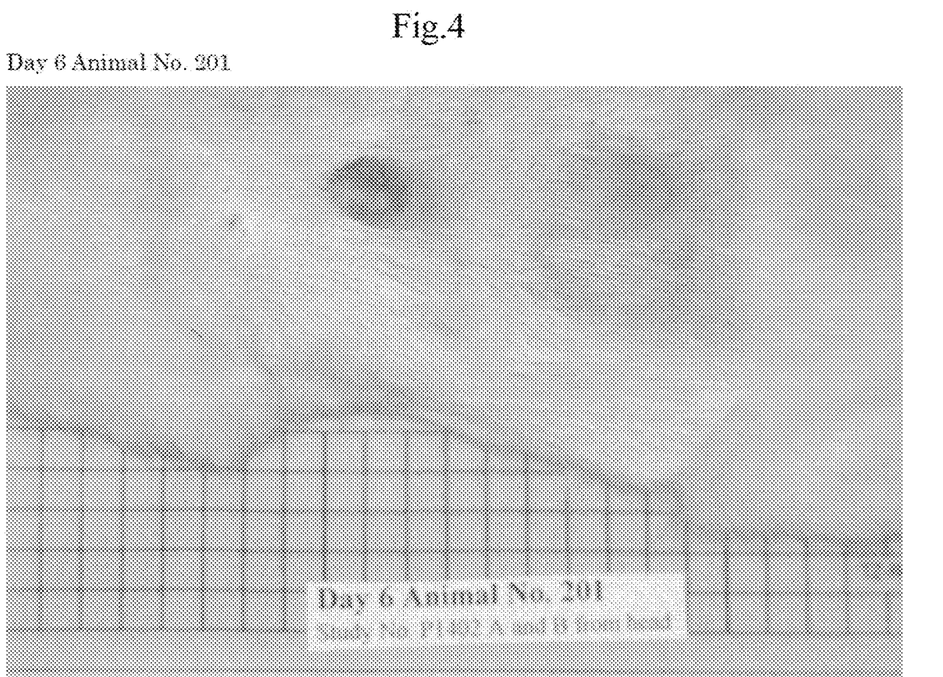
FIG. 4 is a photographic image showing the condition of a burn injury site on day 6.
Figure 5:
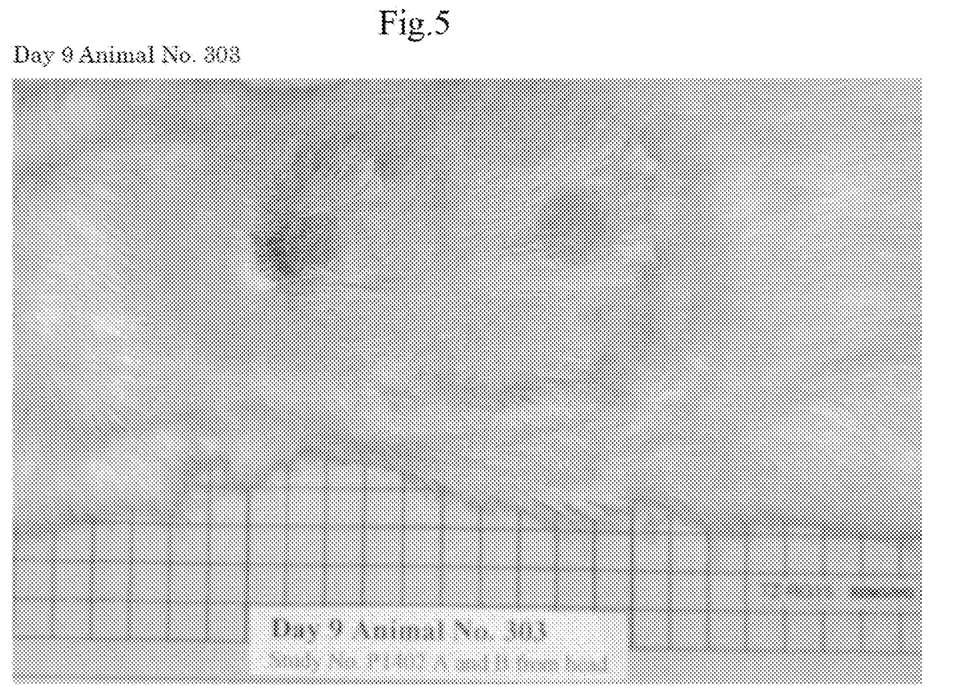
FIG. 5 is a photographic image showing the condition of a burn injury site on day 9.

The evaluation results are shown in FIGS. 1 to 5 and Table 1. FIG. 1 is a graph showing scores of the skin conditions on day 3, day 6, and day 9 of burn injury sites to which the nonwoven fabrics A and B were applied. FIGS. 2 to 5 are photographic images each showing the condition of a burn injury site on day 0 (immediately after the formation of the burn injury site), day 3, day 6, or day 9. In FIGS. 3 to 5, the left side is a burn injury site from which the nonwoven fabric A has been removed, and the right side is a burn injury site from which the nonwoven fabric B has been removed, as seen from the front.

TABLE 1

| Test Group A | Day 3 | | Test Group B | Day 6 | | Test Group C | Day 9 | |
|---|---|---|---|---|---|---|---|---|
| Animal No. | Nonwoven Fabric A | Nonwoven Fabric B | Animal No. | Nonwoven Fabric A | Nonwoven Fabric B | Animal No. | Nonwoven Fabric A | Nonwoven Fabric B |
| 101 | 1 | 1 | 201 | 4 | 1 | 301 | 4 | 3 |
| 102 | 2 | 2 | 202 | 4 | 1 | 302 | 4 | 3 |
| 103 | 2 | 1 | 203 | 2 | 2 | 303 | 4 | 3 |
| 104 | 1 | 1 | 204 | 2 | 2 | 304 | 3 | 4 |
| 105 | 2 | 1 | 205 | 2 | 2 | 305 | 3 | 4 |
| n | 5 | 5 | n | 5 | 5 | n | 5 | 5 |
| Average | 1.6 | 1.2 | Average | 2.8 | 1.6 | Average | 3.6 | 3.4 |
| Standard Error | 0.2 | 0.2 | Standard Error | 0.5 | 0.2 | Standard Error | 0.2 | 0.2 |

As shown in FIG. 1 and Table 1, the scores of both the nonwoven fabric A and the nonwoven fabric B increased from day 3 to day 9 after the formation of burn injuries. The score of the nonwoven fabric A increased over time: day 3, 1.6; day 6, 2.8; and day 9, 3.6. The score of the nonwoven fabric B increased but at a lower level than the nonwoven fabric A: day 3, 1.2; day 6, 1.6; and day 9, 3.4. The score of the nonwoven fabric A was 4 (crusting) on day 6, and the score of the nonwoven fabric B was from 1 to 2 on day 6. The score of the nonwoven fabric B tended to be lower than that of the nonwoven fabric A ($P=0.0753$, Wilcoxon test).

Although the scores of both the nonwoven fabrics A and B were from 3 to 4 on day 9, the score of the nonwoven fabric B tended to be lower than that of the nonwoven fabric A.

As shown in FIGS. 2 and 4, two burn injury sites showed no difference immediately after being formed and showed a big difference on day 6. The skin condition was better at the right burn injury site, to which the nonwoven fabric B had been applied, than at the left burn injury site, to which the nonwoven fabric A had been applied. As shown in FIGS. 3 and 5, on day 3 and on day 9, the skin condition was better at the right burn injury site, to which the nonwoven fabric B had been applied, than at the left burn injury site, to which the nonwoven fabric A had been applied.

The above results show that the application of the nonwoven fabric B ameliorates the condition of skin having a burn injury. In other words, the glycerol alkyl ester has an external wound-healing effect.

Production of Film 1

Synthesis of Prepolymer

In a four-necked flask equipped with a stirrer, a thermometer, a reflux condenser, and a nitrogen inlet tube, 24.9 parts by mass of 1,4-BIC3 (1,4-bis(isocyanatomethyl)cyclohexane 3) described in WO 2009/051114 and 100.0 parts by mass of vacuum-dehydrated PEG2000U (polyethylene glycol having a number average molecular weight of 2,000, NOF Corporation) were placed and stirred in a nitrogen atmosphere at 80° C. for 1 hour. To the mixture, 0.015 part by mass of a 4% by mass dilute solution of bismuth octoate (catalyst, Neostann U-600 (trade name) available from Nitto Kasei Co., Ltd.) in DINA (J-PLUS Co., Ltd.) was added and allowed to react to an isocyanate group content of 5.23% by mass to obtain an isocyanate-group-terminated polyurethane prepolymer (hereinafter referred to as a prepolymer for short).

Synthesis of Thermoplastic Polyurethane

One hundred parts by mass of the prepolymer preadjusted to be 80° C., 1.06 parts by mass of GA-80 (heat stabilizer available from Sumitomo Chemical Co., Ltd.), 0.32 part by mass of TINUVIN234 (UV absorber available from BASF), and 0.32 part by mass of ADK STAB LA-72 (HALS available from ADEKA Corporation) were placed in a stainless-steel container and mixed with stirring at 1,000 rpm for about 2 minutes using a high-speed disper, thereby providing a mixed solution. To the mixed solution, 5.34 parts by mass of 1,4-BD preadjusted to be 80° C., serving as a chain extender, and 0.013 part by mass of a 4% by mass dilute solution of bismuth octoate (catalyst, Neostann U-600 (trade name) available from Nitto Kasei Co., Ltd.) in DINA (J-PLUS Co., Ltd.) were added and mixed with stirring at 1,000 rpm for about 10 minutes using the high-speed disper.

The reaction mixture was then poured into a stainless-steel vat preadjusted to be 150° C., and allowed to react at 150° C. for 1 hour and then at 100° C. for 23 hours to obtain a thermoplastic polyurethane.

The thermoplastic polyurethane was then taken out of the vat and cured for 7 days under constant temperature and constant humidity conditions at room temperature of 23° C. and a relative humidity of 55%.

The thermoplastic urethane obtained was cut into cubes with a bale cutter, and the cubed resin was ground with a grinder. The ground pellets were dried at 80° C. for 24 hours under a stream of nitrogen. Using a single-screw extruder (Model SZW40-28MG, Technovel Corporation), a strand was extruded at a cylinder temperature in a range of from 150° C. to 245° C., and the strand was cut to obtain thermoplastic polyurethane pellets. The pellets were further dried at 80° C. for 24 hours under a stream of nitrogen.

Film Formation

The thermoplastic polyurethane thus obtained (thermoplastic polyurethane pellets predried in a nitrogen atmosphere to a water content of 120 ppm) was used as a urethane resin, and POEM V-100 (trade name) glycerol stearate available from Riken Vitamin Co., Ltd. was used as a glycerol alkyl ester. First, 1 part by mass of the glycerol alkyl ester was added to 100 parts by mass of the urethane resin and mixed to obtain a mixture. A single-screw extruder (trade name: SZW20, Technovel Corporation) having a bore of 20 mm and equipped with a coat hanger die having a width of 150 mm, and an apparatus equipped with a stainless-steel casting roll were used for the extrusion molding of a film. The screw rotation speed was set to 20 rpm. The cylinder temperature was set to 235° C. The die temperature was set to 225° C. The temperature of cooling water for the casting roll was set to about 22° C. The rotation speed of the roll was set to 3 m/min. The mixture was extrusion molded while nitrogen was fed through a hopper, thereby providing a 40-μm-thick polyurethane film (film 1) to which glycerol stearate was added.

Production of Film 2

The same production procedure as for the film 1 was repeated except that 3 parts by mass of the glycerol alkyl ester was added to 100 parts by mass of the urethane resin to obtain a 40-μm-thick polyurethane film (film 2) to which glycerol stearate was added.

Using the films 1 and 2 obtained as described above and a 40-μm-thick polyurethane film (film 3) obtained in the same manner as for the film 1 except that no glycerol alkyl ester was added, the healing effect was evaluated by the animal testing described below.

Animal Experiment

In this animal testing, the films 1 to 3 were applied to burn injury sites on the backs of rats, and the healing effects by the application of the films 1 to 3 were evaluated. For comparison, a burn injury site was left untreated, and the development of the untreated site was observed. The details of the experiment will be described below.

The back of a rat was depilated. In the depilated portion, hot water at 80° C. was brought into contact for 5 seconds to form two burn injury sites. To the two burn injury sites, the film 1 (about 2 cm×2 cm) and the film 2 (about 2 cm×2 cm) were applied, and occlusive patching was performed using moisture-permeable adhesive flexible bandage (Dermapore, ALCARE Co., Ltd.) and adhesive flexible bandage (Silkytex 3, ALCARE Co., Ltd). On days 3, 6, and 9 after the application of the films 1 and 2, the films were removed, and the healing effect was evaluated.

Furthermore, two burn injury sites were formed on the back of another rat in the same manner as described above. The film 3 (about 2 cm×2 cm) was applied to one burn injury site, and occlusive patching was performed in the same manner as described above. The other burn injury site was left untreated. On days 3, 6, and 9 after the application of the film 3, the film was removed, and the healing effect was evaluated. On days 3, 6, and 9, the development of the untreated site was observed.

Test Group Configuration

Two burn injury sites were each formed on 30 rats. For 15 rats among them, the film 1 and the film 2 were applied to each two burn injury sites, and these rats were divided into test groups A, B, and C each including 5 rats. For the other 15 rats, the film was applied to one burn injury site, while the other burn injury site was left untreated, and these rats were divided into test groups A, B, and C each including 5 rats. On day 3, the films 1 to 3 on the rats of test group A were removed, and the skin conditions were assessed, and the development of the untreated site was observed to assess the skin condition. On day 6, the films 1 to 3 on the rats of test group B were removed, and the skin conditions were assessed, and the development of the untreated site was observed to assess the skin condition. On day 9, the films 1 to 3 on the rats of test group C were removed, and the skin conditions were assessed, and the development of the untreated site was observed to assess the skin condition.

Test group A: percutaneous administration (route of administration), animal No. 101-110 (animal No. 101-105, films 1 and 2 applied; animal No. 106-110, film 3 applied, including untreated site), 10 males Test group B: percutaneous administration (route of administration), animal No. 201-210 (animal No. 201-205, films 1 and 2 applied; animal No. 206-210, film 3 applied, including untreated site), 10 males Test group C: percutaneous administration (route of administration), animal No. 301-310 (animal No. 301-305, films 1 and 2 applied; animal No. 306-310, film 3 applied, including untreated site), 10 males Weighing and Observation on General Condition The animals were weighed at the time of arrival, on the day following the arrival, at the formation of a wound, and at the end of experimentation. General conditions were observed every day.

Grouping, Evaluation Method, and Method of Statistical Analysis

The grouping, the evaluation method, and the method of statistical analysis were the same as described above.

Figure 6:
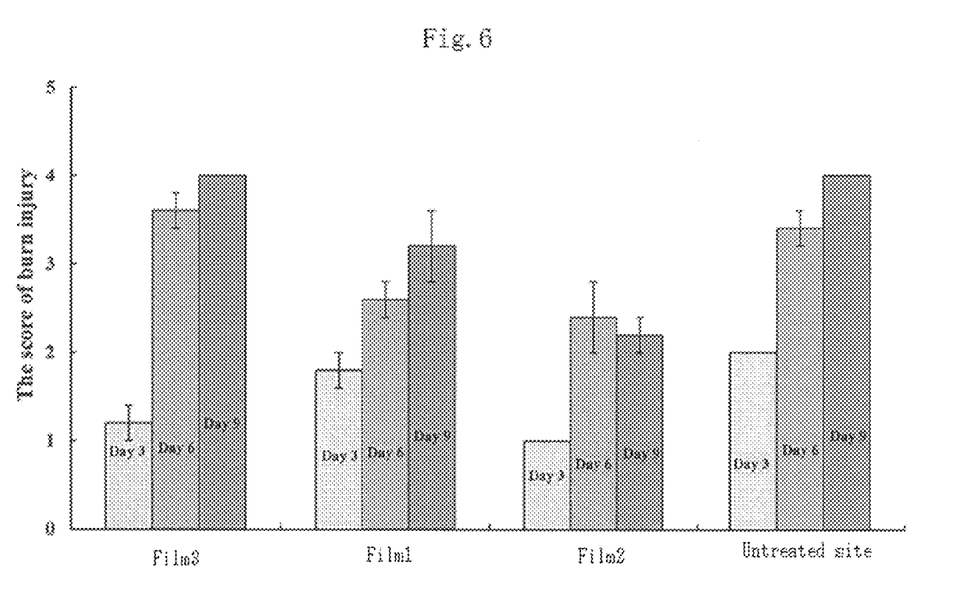
FIG. 6 is a graph showing scores of the skin conditions on day 3, day 6, and day 9 of burn injury sites to which films 1 to 3 were applied and an untreated site.

The evaluation results are shown in FIG. 6 and Table 2. FIG. 6 is a graph showing scores of the skin conditions on day 3, day 6, and day 9 of burn injury sites to which the films 1 to 3 were applied and an untreated site.

TABLE 2

| Test Group A Animal No. | Day 3 | | | | Test Group B Animal No. | Day 6 | | | | Test Group C Animal No. | Day 9 | | | |
|---|---|---|---|---|---|---|---|---|---|---|---|---|---|---|
| | Film 1 | Film 2 | Film 3 | Untreated Site | | Film 1 | Film 2 | Film 3 | Untreated Site | | Film 1 | Film 2 | Film 3 | Untreated Site |
| 101 | 1 | 1 | — | — | 201 | 3 | 2 | — | — | 301 | 4 | 2 | — | — |
| 102 | 2 | 1 | — | — | 202 | 3 | 2 | — | — | 302 | 3 | 2 | — | — |
| 103 | 2 | 1 | — | — | 203 | 2 | 2 | — | — | 303 | 3 | 2 | — | — |
| 104 | 2 | 1 | — | — | 204 | 3 | 4 | — | — | 304 | 2 | 3 | — | — |
| 105 | 2 | 1 | — | — | 205 | 2 | 2 | — | — | 305 | 4 | 2 | — | — |
| 106 | — | — | 1 | 2 | 206 | — | — | 4 | 3 | 306 | — | — | 4 | 4 |
| 107 | — | — | 1 | 2 | 207 | — | — | 4 | 4 | 307 | — | — | 4 | 4 |
| 108 | — | — | 1 | 2 | 208 | — | — | 3 | 3 | 308 | — | — | 4 | 4 |
| 109 | — | — | 2 | 2 | 209 | — | — | 4 | 4 | 309 | — | — | 4 | 4 |
| 110 | — | — | 1 | 2 | 210 | — | — | 3 | 3 | 310 | — | — | 4 | 4 |
| n | 5 | 5 | 5 | 5 | n | 5 | 5 | 5 | 5 | n | 5 | 5 | 5 | 5 |
| Average | 1.8 | 1 | 1.2 | 2.0 | Average | 2.6 | 2.4 | 3.6 | 3.4 | Average | 3.2 | 2.2 | 4.0 | 4.0 |
| Standard Deviation | 0.2 | 0.0 | 0.2 | 0.0 | Standard Deviation | 0.2 | 0.4 | 0.2 | 0.2 | Standard Deviation | 0.4 | 0.2 | 0.0 | 0.0 |

As shown in FIG. 6 and Table 2, the scores of the films 1 and 3 and the untreated increased over time from day 3 to day 9 after the formation of burn injuries. By contrast, the score of the film 2 increased on day 6 after the formation of a burn injury but decreased on day 9.

The scores of the films 1 and 2 were lower than those of the film 3 and the untreated. The score of the film 1 tended to be lower than those of the film 3 and the untreated on day 6 and day 9 (on day 6, P<0.05 as compared to the untreated; on day 9, P=0.0707 as compared to the untreated; Wilcoxon test). The score of the film 2 tended to be lower than those of the film 3 and the untreated on day 3, day 6, and day 9 (on day 6, P=0.0573 as compared to the untreated; on day 9, P<0.01 as compared to the untreated; Wilcoxon test).

The above results show that the application of the films 1 and 2 ameliorates the condition of skin having a burn injury. In other words, the glycerol alkyl ester has an external wound-healing effect.

The disclosure of Japanese Patent Application No. 2014-145189 filed on Jul. 15, 2014, is incorporated herein by reference in its entirety.

All the documents, patent applications, and technical standards mentioned in this specification are incorporated herein by reference to the same extent as if each individual document, patent application, and technical standard was specifically and individually indicated to be incorporated by reference.

The invention claimed is:

1. A method of healing an external wound, the method comprising:

applying an external wound-healing agent to an external wound, or bringing the external wound-healing agent applied to a substrate into contact with an external wound, or bringing a fiber aggregate or a film into contact with an external wound, wherein the external wound-healing agent comprises an active ingredient consisting of a glycerol alkyl ester, or the fiber aggregate or the film each comprises: a thermoplastic resin; and an active ingredient, consisting of the glycerol alkyl ester, wherein the glycerol alkyl ester is represented by the following Formula (I):

and wherein, in Formula (I), one of $R^1$, $R^2$, and $R^3$ is $C_{17}H_{35}CO-$ or $C_{19}H_{39}CO-$, and the others are a hydrogen atom wherein the method does not comprise administration of any additional active ingredients; and.

2. The method of healing an external wound according to claim 1, wherein the glycerol alkyl ester is glycerol stearate.

3. The method of healing an external wound according to claim 1, wherein the amount of the glycerol alkyl ester represented by the Formula (I) is from 0.05 part by mass to 5 parts by mass with respect to 100 parts by mass of the external wound-healing agent.

4. The method of healing an external wound according to claim 1, wherein the thermoplastic resin is at least one resin selected from the group consisting of olefin resins, urethane resins, amide resins, ester resins, acrylic resins, styrene resins, and carbonate resins.

5. The method of healing an external wound according to claim 4, wherein the thermoplastic resin is an olefin resin.

6. The method of healing an external wound according to claim 5, wherein the olefin resin is at least one of an ethylene copolymer or a propylene copolymer.

7. The method of healing an external wound according to claim 1, wherein the fiber aggregate is a nonwoven fabric.

8. The method of healing an external wound according to claim 1, wherein the amount of the glycerol alkyl ester represented by the Formula (I) is from 0.05 part by mass to 5 parts by mass with respect to 100 parts by mass of the thermoplastic resin.

9. A method of healing an external wound, the method comprising:
   applying an external wound-healing agent to an external wound, or bringing the external wound-healing agent applied to a substrate into contact with an external wound, or bringing a fiber aggregate or a film into contact with an external wound,
   wherein the external wound-healing agent comprises, as an active ingredient, a glycerol alkyl ester, or the fiber aggregate or the film each comprises: a thermoplastic resin; and, as an active ingredient, the glycerol alkyl ester, wherein the glycerol alkyl ester is represented by Formula (I):

and
   wherein in Formula (I), one of $R^1$, $R^2$, and $R^3$ is $C_{19}H_{39}CO-$, and the others are a hydrogen atom.

* * * * *